United States Patent
Heydrich et al.

(10) Patent No.: US 8,414,744 B2
(45) Date of Patent: Apr. 9, 2013

(54) CONTINUOUS PROCESS FOR PREPARING MENTHOL IN PURE OR ENRICHED FORM

(75) Inventors: Gunnar Heydrich, Limburgerhof (DE); Gabriele Gralla, Mannheim (DE); Klaus Ebel, Lampertheim (DE); Wolfgang Krause, Brühl-Rohrhof (DE); Nawid Kashani-Shirazi, Ilvesheim (DE)

(73) Assignee: BASF SE (DE)

( * ) Notice: Subject to any disclaimer, the term of this patent is extended or adjusted under 35 U.S.C. 154(b) by 0 days.

(21) Appl. No.: 12/677,688

(22) PCT Filed: Jul. 23, 2008

(86) PCT No.: PCT/EP2008/059657
§ 371 (c)(1),
(2), (4) Date: Mar. 11, 2010

(87) PCT Pub. No.: WO2009/033870
PCT Pub. Date: Mar. 19, 2009

(65) Prior Publication Data
US 2010/0206712 A1    Aug. 19, 2010

(30) Foreign Application Priority Data
Sep. 11, 2007  (EP) .................................. 07116155

(51) Int. Cl.
*B01D 3/14* (2006.01)
(52) U.S. Cl.
USPC ................. 203/5; 202/160; 203/99; 568/829

(58) Field of Classification Search ................... 203/2, 5, 203/47, 99, 74–78, 80; 202/160, 161, 189
See application file for complete search history.

(56) References Cited

U.S. PATENT DOCUMENTS

| 826,281 | A | * | 7/1906 | McLaughlin et al. | ........ 534/884 |
| 1,930,411 | A | | 10/1933 | Blagden | |
| 2,471,134 | A | | 5/1949 | Wright | |
| 2,662,052 | A | * | 12/1953 | Bridger et al. | .................. 203/44 |
| 2,827,497 | A | | 3/1958 | Bottoms | |
| 4,230,533 | A | | 10/1980 | Giroux | |

(Continued)

FOREIGN PATENT DOCUMENTS
CA    1222717 A1    6/1987
CA    1242309 A1    9/1988

(Continued)

OTHER PUBLICATIONS http://www.answers.com/topic/uses-of-kudzu-root.*

(Continued)

*Primary Examiner* — Duane Smith
*Assistant Examiner* — Ives Wu
(74) *Attorney, Agent, or Firm* — Novak Druce Connolly Bove + Quigg LLP

(57) ABSTRACT

The present invention relates to a continuous process for preparing racemic or optically active menthol in pure or enriched form by distillatively separating menthol from substance mixtures which comprise essentially menthol and diastereomers thereof. This distillatiive separation is performed in a dividing wall column with 50 to 300 theoretical plates and one or more side draw points at an absolute operating pressure of 5 to 500 mbar.

16 Claims, 1 Drawing Sheet

U.S. PATENT DOCUMENTS

| | | | |
|---|---|---|---|
| 4,874,473 A | 10/1989 | Arlt et al. | |
| 5,785,819 A * | 7/1998 | Kaibel et al. | 202/158 |
| 6,387,222 B1 * | 5/2002 | Tragut et al. | 203/2 |
| 7,211,698 B2 * | 5/2007 | Heydrich et al. | 568/600 |
| 7,709,688 B2 | 5/2010 | Bergner et al. | |
| 2002/0128910 A1 | 9/2002 | Sakuma | |
| 2003/0106786 A1 | 6/2003 | Kaibel et al. | |
| 2008/0214877 A1 | 9/2008 | Rauls et al. | |

FOREIGN PATENT DOCUMENTS

| | | |
|---|---|---|
| DE | 568085 C | 1/1933 |
| DE | 1189073 B | 3/1965 |
| DE | 3522234 A1 | 1/1987 |
| DE | 10223974 A1 * | 12/2003 |
| DE | 10223974 A1 * | 12/2003 |
| DE | 10223974 A1 | 12/2003 |
| DE | 10330934 A1 | 2/2005 |
| DE | EP-1514955 A1 * | 3/2005 |
| DE | EP 1514955 A1 * | 3/2005 |
| DE | 102005040655 A1 | 3/2007 |
| EP | 0122367 A2 | 10/1984 |
| EP | 0126288 A2 | 11/1984 |
| EP | 0133510 A1 | 2/1985 |
| EP | 0242778 A1 | 10/1987 |
| EP | 0640367 A1 | 3/1995 |
| EP | 0780147 A2 | 6/1997 |
| EP | 1 225 163 A2 | 7/2002 |
| EP | 1514955 A1 | 3/2005 |
| GB | 285394 A | 7/1928 |
| GB | 285833 A | 5/1929 |
| GB | 826281 A | 12/1959 |
| JP | 2002-212121 A | 7/2002 |
| JP | 2002-334201 A | 11/2002 |
| JP | 2003-532720 A | 11/2003 |
| WO | WO-2006/056435 A1 | 6/2006 |

OTHER PUBLICATIONS http://www.livestrong.com/article/157874-peppermint-oil-components/.*

Kaibel, Gerd, "Distillation Columns with Vertical Partitions", Chem. Eng. Technol., vol. 10, (1987), pp. 92-98.

Kaibel, et al., "Gestaltung Destillativer Trennungen unter Einbeziehung Thermodynamischer Gesichtspunkte", Chem.-Ing.-Tech., vol. 61, No. 1, (1989), pp. 16-25.

Knot, Michelle, "Designs on Mixing", Process Engineering, vol. 2, (1993), pp. 33-34.

Lestak, et al., "Heat Transfer Across the Wall of Dividing Wall Columns", Institution of Chemical Engineers, (1994), pp. 639-644.

Lestak, et al,, "Advanced Distillation Saves", Chemical Engineering, vol. 102, (1997), pp. 72-76.

Wolff, et al., "Operation of Integrated Three-Product (Petlyuk) Distillation Columns", Ind. Eng. Chem. Res., vol. 34, (1995), pp. 2094-2103.

"Separation of DL-menthol from a Racemic Mixture of Menthols by Vacuum Distillation", XP002472792, (2001).

U.S. Appl. No. 12/666,478, filed Dec. 23, 2009, Heydrich et al.

* cited by examiner

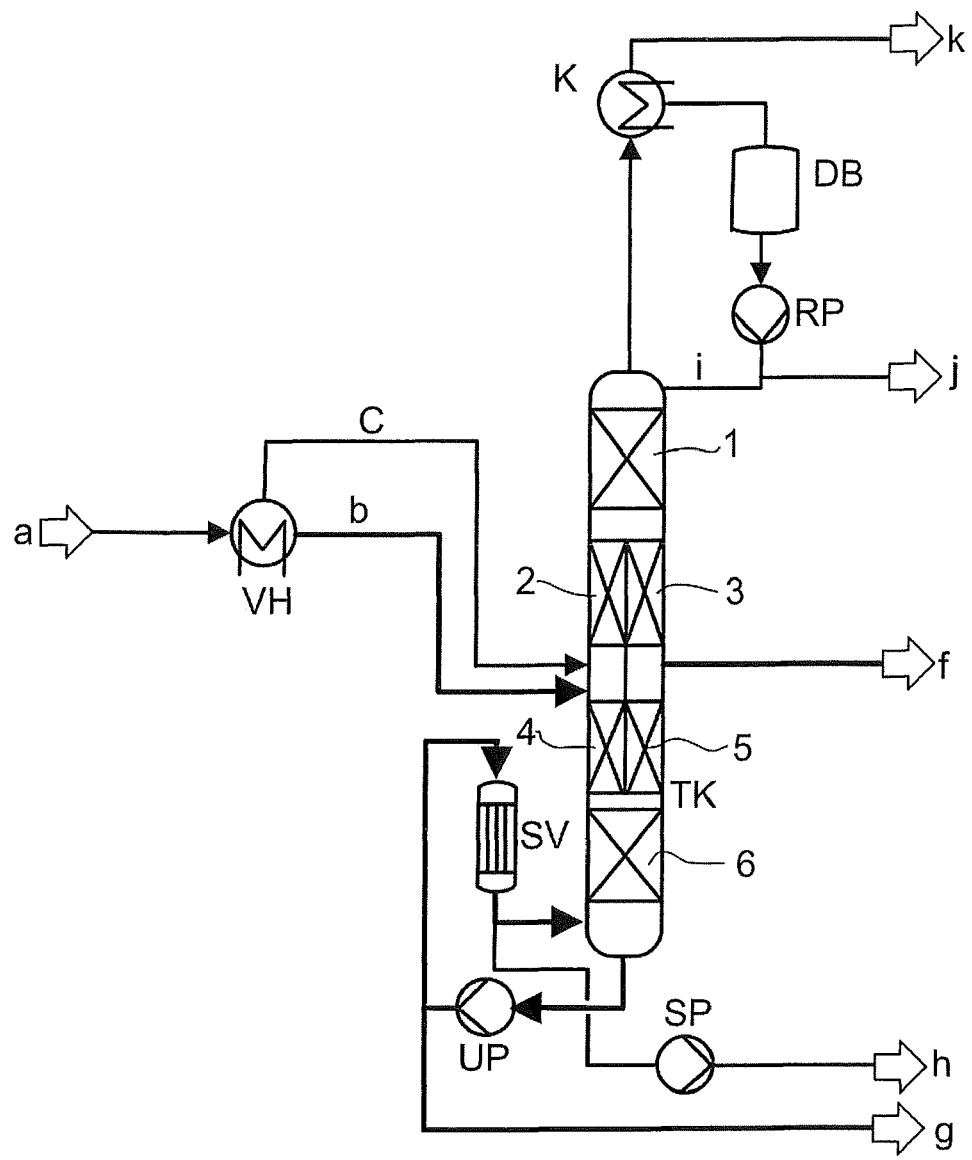

CONTINUOUS PROCESS FOR PREPARING MENTHOL IN PURE OR ENRICHED FORM

CROSS-REFERENCE TO RELATED APPLICATIONS

This application is a national stage application (under 35 U.S.C. §371) of PCT/EP2008/059657, filed Jul. 23, 2008, which claims benefit of European application 07116155.8, filed Sep. 11, 2007.

BACKGROUND OF THE INVENTION

The present invention relates to a continuous process for preparing racemic or optically active menthol, specifically L-menthol, in pure or enriched form by distillatively separating menthol from substance mixtures which comprise essentially menthol. This distillative separation is conducted in a dividing wall column.

Menthol, especially L-menthol, is one of the most important aroma chemicals globally and, owing to its cooling properties and to the fresh peppermint aroma, is used in a multitude of products.

The literature describes various purification processes for menthol. For instance, the person skilled in the art is aware, in addition to fractional distillation with and without steam, as described, for example, in DE 568 085 or DE 1 189 073 and U.S. Pat. No. 1,930,411, JP 27003884 or JP 32009869, of extraction processes and crystallization processes.

These processes are sometimes also used in combination, for example as combinations of crystallization and fractional distillation, or else in combination with chemical reactions or derivatizations.

GB 285,394 relates to a process for preparing racemic menthol by hydrogenating thymol, fractional distillation of the mixtures obtained therefrom and subsequent freezing of neomenthol out of the menthol fractions.

GB 285,833 describes a process for preparing thymol by fractional distillation of mixtures which have been obtained from the condensation of cresol with acetone, and, as well as thymol, comprise isomeric methylisopropylphenols.

U.S. Pat. No. 2,827,497 discloses a process in which diastereomer mixtures of menthol obtained by fractional distillation and fractional crystallization are subjected to an oxidation and then purified further by another fractional distillation.

EP 0 242 778 describes a process for separating diastereomer mixtures, including mixtures of menthol, isomenthol, neomenthol and neoisomenthol, by extractive distillation, i.e. by distillation with addition of more specific assistants, for example succinamide.

The processes described usually have the disadvantage that assistants are used (steam or extractive distillation), or solids are obtained. The fractional batchwise distillations are disadvantageous usually with regard to their yield of product of value, since the product is thermally stressed for a longer period.

EP 1 514 955 relates to a process for distillative workup of the electrolysis output of the electrochemical oxidation of 1,1,2,2-tetramethoxyethane with methanol to give trimethyl orthoformate in a liquid electrolyte, wherein a dividing wall column with 30 to 150 theoretical plates is used.

DE 103 30 934 discloses a process for continuously isolating citronellal or citronellol from a crude mixture comprising at least one of these compounds by rectification. Preference is given to using those starting mixtures which are obtained by partial hydrogenation of citral or citronellal.

DE 102 23974 relates to a process for continuously isolating two stereoisomeric isoprenoid alcohols, specifically nerol and geraniol, from a crude mixture by rectification, wherein the crude mixture is introduced laterally into a feed column, at least one draw column coupled to the feed column is provided, and a first and second isoprenoid alcohol are drawn off from the draw column. The feed and draw columns are coupled such that there is no cross-mixing of vapor and condensate at least in the region of the draw point of the isoprenoid alcohols.

The distillative purification of menthol, specifically of L-menthol to free it of its neoiso- and isomenthol diastereomers, is typically very complex especially owing to the very small boiling point difference of approx. 2° C. at ambient pressure.

BRIEF SUMMARY OF THE INVENTION

Proceeding from this prior art, it was an object of the present invention to provide a process for preparing very pure or enriched menthol proceeding from mixtures which, as well as menthol, comprise undesired diastereomers of menthol and possibly also isopulegol or isomers thereof and possibly also menthones. The process should especially be suitable for preparing pure or enriched menthol proceeding from mixtures in which menthol is already present as the predominant main component and which comprise the undesired components mentioned only to a very minor extent or as impurities. This is possible only with difficulty and with high yield losses by the known processes. The process should be performable with a low level of apparatus complexity, in an economically viable manner and on the industrial scale, while especially leading to only a small degree of formation of decomposition products or by-products, i.e. afford the desired product in high purity and in maximum yield.

The object was achieved in accordance with the invention by the provision of a continuous process for preparing racemic or optically active menthol of the formula (I)

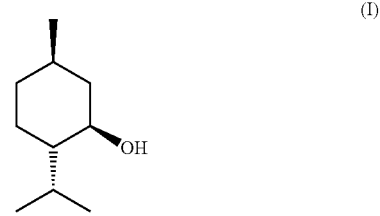

in pure or enriched form by distillatively separating racemic or optically active menthol from substance mixtures comprising racemic or optically active menthol and diastereomers of menthol, wherein the distillative separation is performed in a dividing wall column with 50 to 300 theoretical plates and one or more side draw points at an absolute operating pressure of 5 to 500 mbar.

A BRIEF DESCRIPTION OF THE FIGURE

FIG. 1 illustrates a plant utilizing the process according to the invention.

DETAILED DESCRIPTION OF THE INVENTION

The starting materials used to perform the process according to the invention are substance mixtures which comprise racemic or optically active menthol, preferably optically active menthol, more preferably L-menthol and diastereomers of menthol.

Diastereomers of menthol include the compounds neomenthol of the formula (V), neo-isomenthol of the formula (VI) and isomenthol of the formula (VII)

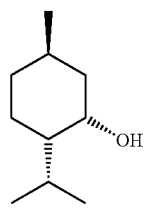
(V)

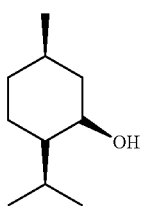
(VI)

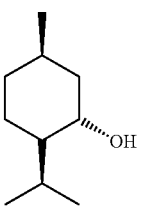
(VII)

which, according to the type of mixture which serves as the starting material, may be in racemic or nonracemic, i.e. optically active, form. The diastereomers mentioned may be present in the substance mixtures for use in accordance with the invention individually or in the form of mixtures. The substance mixtures for use as a starting material in the process according to the invention comprise, as well as menthol of the formula (I) in racemic or optically active form, at least one of the diastereomers of the formula (V), (VI) or (VII), but typically a mixture of two or all three of the diastereomers mentioned.

In the process according to the invention, it is preferably also possible to use those substance mixtures which comprise, as well as the aforementioned diastereomers of menthol, also isopulegol of the formula (II)

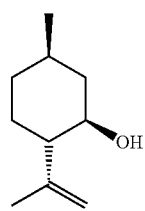
(II)

and/or diastereomers thereof, with or without menthone of the formula (III) and/or isomenthone of the formula (IV)

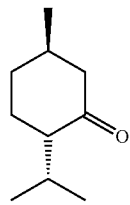
(III)

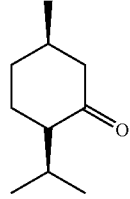
(IV)

The compounds mentioned may, according to the type, origin or preparation process of the substance mixture used in each case, be present in racemic or optically active form.

Diastereomers of isopulegol of the formula (II), especially L-isopulegol, include neoisopulegol of the formula (VIII), neoisoisopulegol of the formula (IX) and isoisopulegol of the formula (X)

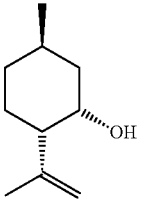
(VIII)

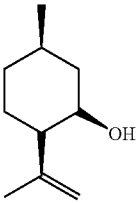
(IX)

(X)

which may likewise be present, according to the type of mixture which serves as the starting material, in racemic or nonracemic form.

A preferred embodiment of the process according to the invention relates to the preparation of L-menthol in pure or enriched form by distillatively separating L-menthol from substance mixtures comprising L-menthol and diastereomers of menthol of the formulae (V), (VI) and/or (VII), with or without isopulegol of the formula (II) and/or diastereomers thereof of the formulae (VIII), (IX) and/or (X), and with or without menthone of the formula (III) or isomenthone of the formula (IV).

Suitable feedstocks for performing the process according to the invention are substance mixtures which comprise racemic or optically active menthol, preferably L-menthol in optically active form, preferably those which consist predominantly of racemic or optically active menthol, preferably L-menthol. Among these, preference is given to those substance mixtures which comprise at least 80% by weight or better 85 or even better 90% by weight to 99.9% by weight, more preferably 95 to 99.8% by weight and most preferably at least 96% by weight, 97% by weight or most preferably at least 98% by weight to 99.7% by weight, 99.6% by weight or most preferably to 99.5% by weight of racemic or optically active menthol, preferably L-menthol, and additionally a small proportion, i.e. a proportion of up to 20, preferably of 0.1 up to 10% by weight and more preferably of 0.2 up to 5% by weight, especially preferably of 0.3 or better 0.4% by weight up to 2.5% by weight, even more preferably up to 1.5% by weight, better up to 1% by weight and most preferably up to 0.5% by weight, of further components, for example diastereomers of menthol, by-products such as isopulegol or diastereomers thereof, or menthone or isomenthone or other impurities, for example solvent residues or water.

In the case of use of substance mixtures which comprise menthol in optically active form, preferably L-menthol, it is present typically in an enantiomeric excess of 90% ee or higher, preferably 95% ee, more preferably 97% ee or even more preferably 98% ee or higher, i.e. up to 100% ee or preferably up to 99.9% ee. Correspondingly optically active menthol, preferably L-menthol, in pure or enriched form is obtained from these substance mixtures in the process according to the invention, the enantiomeric excess of the product obtained generally corresponding at least very substantially to the enantiomeric excess of the menthol in the substance mixture used. In the case of use of substance mixtures comprising racemic menthol, racemic menthol of the formula (I) in pure or enriched form is obtained in accordance with the invention.

In a preferred embodiment of the process according to the invention, the starting material used is a substance mixture which has an enantiomeric excess of more than 99.4% ee. In a further preferred embodiment of the process according to the invention, the starting material used is a substance mixture which consists to an extent of at least 98% by weight of menthol (L- or else D-menthol, preferably L-menthol) and to a total extent of up to 2% by weight (based in each case on the mixture) of diastereomers of menthol and/or isopulegol and diastereomers thereof (each in the d or l form) and/or isomenthone or menthone and/or other components such as alcohols, ketones, aldehydes, hydrocarbons or water, the mixture of menthone and/or isomenthone and the content of other components each being less than 1% by weight (based on the mixture).

A preferred feedstock is synthetic menthol, preferably L-menthol in optically active form, especially that prepared by hydrogenating isopulegol or L-isopulegol. Isopulegol, specifically L-isopulegol, can in turn be obtained by purifying synthetic isopulegol by crystallization, especially by melt crystallization, as described, for example, in DE 10 2005 040 655.

In addition, it is also possible to use mixtures of menthol and diastereomers of menthol which have been prepared by other synthetic routes, for example those as obtainable by the hydrogenation of thymol.

Additionally suitable is commercial L-menthol from natural plant sources, for example that obtained, for example, from Mentha arvensis.

The inventive distillative removal is typically performed by separating the menthol used, preferably L-menthol-comprising substance mixture, into one or more low boiler, medium boiler and high boiler fraction or fractions in each case, and continuously withdrawing menthol, preferably L-menthol in pure or enriched form, in liquid or gaseous form as a medium boiler fraction at the side draw point of the dividing wall column used.

The process according to the invention is accordingly also a continuous process for isolating menthol, preferably L-menthol, preferably a continuous process for isolating menthol in pure or enriched form by distillatively separating menthol from substance mixtures comprising menthol and diastereomers thereof as described above, wherein the distillative separation is performed in a dividing wall column with 80 to 200 theoretical plates and one or more side draw points at an absolute operating pressure of 5 to 500 mbar.

The dividing wall column for use in accordance with the invention has a total number of plates of 50 to 300, preferably 100 to 200 and most preferably 120 to 180 theoretical plates, and one or more side draw points, preferably 1 to 3, especially 1 or 2, and most preferably 1 side draw point or side draw points.

The process according to the invention is performed at an absolute operating pressure in the dividing wall column of 5 to 500 mbar, preferably of 10 to 200 mbar, more preferably of 20 to 120 mbar and most preferably of 20 to 100 mbar, and especially preferably at an absolute operating pressure of 40 to 100 mbar. Preference is given to operating the dividing wall column in such a way that the absolute top pressure is 10 to 100 mbar, particularly preferably 10 to 80 mbar, very particularly preferably 10 to 60 mbar, even more preferably 20 to 60 mbar and especially preferably 40 to 60 mbar. Likewise preferably, the dividing wall column is operated in such a way that the absolute bottom pressure is 20 to 500 mbar, more preferably 30 to 200 mbar or better to 100 mbar, even more preferably 40 to 200 mbar or better to 100 mbar and most preferably 50 to 100 mbar.

The reflux ratio when performing the process according to the invention can be varied within wide limits and is typically about 5:1 to about 2000:1, preferably about 20:1 to 1000:1 and more preferably about 50:1 to about 500:1. Also advantageous is a dephlegmator method, i.e. only the return stream is condensed in the top condenser of the column and fed back to the column. In such an energetically favorable case of partial condensation, the top product to be discharged is obtained exclusively in the aftercooler, which can be operated at lower temperature. It is advantageous in this context to provide a heat carrier circulation system such that the temperature of the cooling medium in the aftercooler can be controlled within a range from 5° C. to about 50° C., in order, if appropriate, to be able to remelt solids formed by desublimation from time to time.

For this reason, it is also advantageous to provide a means of feeding the main condenser and/or the postcondenser of the column with a heat carrier medium (cooling medium) whose temperature can be controlled from 0 to 60° C., preferably from 20 to 60° C. For this purpose, for example, water can be pumped in circulation through the heat exchanger with the aid of a centrifugal pump, and a temperature control system can be used if required to feed cold or hot water into this pumped circulation system. It will be appreciated that electrical heating of this circuit with a flow heater incorporated into the circuit is also possible, or conventional heating with steam.

By virtue of the process according to the invention, menthol of the formula (I), preferably L-menthol in pure or enriched form, is obtainable. The term "menthol in enriched form" is understood to mean menthol, preferably L-menthol-containing substance mixtures, which have a higher content of menthol or L-menthol than the substance mixture which comprises menthol or preferably L-menthol and is used in each case in accordance with the invention. The term "menthol in enriched form" is preferably understood to mean that menthol, preferably L-menthol, which has a purity, i.e. a content, of more than 80 to 99.5% by weight, preferably of 85 to 99.5% by weight, more preferably of 90 or even more preferably of 95% by weight to 99.5% by weight. The process according to the invention also enables the preparation of menthol, preferably L-menthol, in pure form. The term "menthol in pure form" is understood to mean menthol, preferably L-menthol, with a content of greater than or equal to 99% by weight, preferably greater than or equal to 99.1% by weight, preferably of at least 99.2% by weight, further preferably of at least 99.3% by weight, even more preferably of at least 99.4% by weight and especially preferably of at least 99.5% by weight, again preferably of at least 99.6% by weight, further preferably of at least 99.7% by weight and most preferably of 99.8% by weight to 99.99% by weight, preferably to 99.98% by weight, more preferably to 99.97% by weight, even more preferably to 99.96 and most preferably to 99.95% by weight. The figures in % by weight, like all figures in % by weight in the context of the present invention, are based on the total amount of the particular mixture.

The feed, i.e. the substance mixture for use, can be conducted in liquid or gaseous form into the dividing wall column and be separated there into a top and bottom fraction, and one or more side outputs, preferably into one side output. In one side output, the menthol product of value, preferably L-menthol, is obtained in the desired purity, i.e. in enriched or pure form. In a particular embodiment of the process according to the invention, a postcondenser is connected downstream of the top condenser of the column, and, as detailed above, is cooled with a cooling liquid whose temperature can be controlled within the temperature range from 0 to 60° C., preferably from 20 to 60° C. (for example with glycol-containing water), and a low-menthol low boiler fraction is obtained therein.

For the continuous distillative fractionation of multisubstance mixtures, according to the prior art, various process variants are in use. In the simplest case, the feed mixture is fractionated into two fractions, a low-boiling top fraction and a high-boiling bottom fraction. In the case of separation of feed mixtures into more than two fractions, more than one distillation column has to be used according to this process variant. In order to limit the apparatus complexity, columns with liquid or vaporous side draws are used if possible in the separation of multisubstance mixtures. However, the possible use of distillation columns with side draws is greatly restricted by the fact that, according to the prior art, the products withdrawn at the side draw points are never completely pure. In the case of side withdrawals in the rectifying section, which are typically in liquid form, the side product still comprises proportions of low-boiling components which should be removed via the top. The same applies to side withdrawals in the stripping section, which are usually in vaporous form, in which the side product also comprises high boiler components. The use of conventional side draw columns is therefore restricted to cases in which contaminated side products are permissible.

One means of remedy is offered by dividing wall columns. This column type is described, for example, in U.S. Pat. No. 2,471,134; U.S. Pat. No. 4,230,533; EP 0 122 367; EP 0 126 288; EP 0 133 510; Chem. Eng. Technol. 10 (1987) 92-98; Chem.-Ing.-Tech. 61 (1989) No. 1, 16-25; Gas Separation and Purification 4 (1990) 109-114; Process Engineering 2 (1993) 33-34; Trans IChemE 72 (1994) Part A 639-644 and Chemical Engineering 7 (1997) 72-76.

In the case of this design, it is possible to withdraw side products likewise in pure form. In the middle region, above and below the feed point and the side withdrawal, is mounted a dividing wall which seals the feed section from the withdrawal section and prevents cross-mixing of liquid and vapor steams in this column section. As a result, the number of distillation columns required in total is reduced for the separation of multisubstance mixtures. Since this column type constitutes an apparatus simplification of thermally coupled distillation columns, it additionally also has a particularly low energy consumption. A description of thermally coupled distillation columns, which can be designed in various apparatus configurations, can likewise be found in the abovementioned references in the technical literature. Dividing wall columns and thermally coupled columns offer advantages over the arrangement of conventional distillation columns both in terms of energy demand and of capital costs, and are therefore increasingly being used industrially.

FIG. 1 shows a preferred embodiment of the inventive separation of the menthol-comprising substance mixture for use into a low-menthol top fraction (j), a menthol-rich side fraction (f) and a bottom fraction (g). The menthol-containing feed to the dividing wall column may be in liquid form (b), in gaseous form (c), or in gaseous and liquid form.

The process according to the invention is performed continuously. Accordingly, the substance mixtures which comprise menthol, preferably L-menthol, and are to be used as the starting material are supplied continuously to the dividing wall column, and the products (fractions) and by-products obtained in accordance with the invention are discharged continuously.

A further condenser is typically connected downstream of the column, and the working temperature thereof is 10 to 40 K, preferably 20 to 30 K, below the working temperature of the top condenser of the dividing wall column. With the aid of this, a majority of the low boilers still present in the top stream (k) can be precipitated.

In addition, it may also be advantageous in the case of dividing wall columns to subject the feed stream to a preliminary evaporation and then to feed it to the column in biphasic form or in the form of two streams. This preliminary evaporation is an option particularly when the feed stream comprises relatively large amounts of low boilers. The preliminary evaporation can significantly deburden the stripping section of the column.

The dividing wall columns for use in accordance with the invention can be designed either as packed columns with random packings or structured packings, or as tray columns. In the process according to the invention for preparing menthol in pure or enriched form, it is advisable to use packed columns. In this context, structured sheet metal or fabric packings with a specific surface area of about 100 to 750 $m^2/m^3$, preferably about 350 to 500 $m^2/m^3$, are particularly suitable.

If, as in the case of the present invention, particularly high demands are made on the purities of the products, it is favorable to equip the dividing wall with thermal insulation. A description of the various means of thermal insulation of the dividing wall can be found in EP-A 0 640 367. A double-wall configuration with an intermediate gas space is particularly favorable.

For the control of dividing wall columns and thermally coupled columns, various control strategies have been described. Descriptions can be found in U.S. Pat. No. 4,230, 533; DE 35 22 234; EP 0 780 147; Process Engineering 2 (1993) 33-34 and Ind. Eng. Chem. Res. 34 (1995), 2094-2103.

In the case of separation of multisubstance mixtures into a low boiler fraction, medium boiler fraction and high boiler fraction, there typically exist specifications regarding the maximum permissible proportion of low boilers and high boilers in the medium boiler fraction. In this context, either individual components which are critical for the separating problem, known as key components, or the sum of a plurality of key components, are specified. These key components in the context of the present invention are isomenthol as a high-boiling secondary component, and neomenthol or a mixture of neo- and neoisomenthol as low-boiling secondary components.

Compliance with the specification for the high boilers in the medium boiler fraction can be controlled, for example, via the division ratio of the liquid at the upper end of the dividing wall. The division ratio of the liquid at the upper end of the dividing wall is preferably adjusted such that the concentration of the key components for the high boiler fraction in the liquid at the upper end of the dividing wall makes up 10 to 80%, preferably 30 to 50%, of the value which is to be achieved in the side draw product. The liquid division is preferably adjusted to the effect that more liquid is passed to the feed section in the case of higher contents of key components in the high boiler fraction, and less in the case of lower contents of key components in the high boiler fraction.

The specification for the low boilers in the medium boiler fraction can be controlled correspondingly by the heating output. In this context, for example, the heating output in the evaporator is adjusted such that the concentration of key components in the low boiler fraction in the liquid at the lower end of the dividing wall makes up 10 to 80%, preferably 30 to 50%, of the value which is to be achieved in the side draw product, and the heating output is preferably adjusted to the effect that the heating output is increased at a higher content of key components in the low boiler fraction, and the heating output is reduced at a lower content of key components in the low boiler fraction.

To compensate for perturbations in the feed rate or in the feed concentration, it was additionally found to be advantageous, by means of a corresponding control mechanism, for example by means of suitable control specifications, in the process control system, that the flow rates of the liquids which to the column sections (2), i.e. the rectifying section of the feed section, and (5), i.e. the stripping section of the withdrawal section, cannot fall below 30% of their normal value.

For withdrawal and division of the liquids at the upper end of the dividing wall and at the side withdrawal point, both internal collecting spaces and those arranged outside the column are suitable for the liquid, these assuming the function of a pump reservoir or ensuring a sufficiently high static liquid head, which enable controlled further conduction of liquid by means of control units, for example valves. In the case of use of packed columns, the liquid is first captured in collectors and passed from there into an internal or external collecting space.

In a particularly preferred embodiment, the process according to the invention is performed in a plant as shown schematically in FIG. 1. The preferred embodiment is notable in that a dividing wall column (TK) is used, which has a dividing wall (T) in the longitudinal direction of the column to form an upper combined column region (1), a lower combined column region (6), a feed section (2, 4) with a rectifying section (2) and stripping section (4), and a withdrawal section (3, 5) with a stripping section (3) and rectifying section (5).

According to the invention, the menthol-comprising substance mixture (a) which serves as a feedstock is preferably fed into the middle region of the feed section (2, 4), the menthol, preferably L-menthol, in pure or enriched form is obtained as a liquid or gaseous side draw from the middle region of the withdrawal section (3, 5), and one or more low boiler fractions are removed from the upper combined column region (1), and one or more high boiler fractions from the lower combined column region (6).

The feed stream (a) can be introduced into the column (TK) via a preheater (VH) as a liquid (b), gaseous (c) or partly liquid and partly gaseous stream. The top stream of the column is completely or partially condensed in the condenser (K). In the case of partial condensation (dephlegmator operation), the offgas stream (k) of the top condenser (K) typically still comprises noticeable amounts of condensable low boilers, which can then be precipitated in a postcondenser operated at low temperature.

The top condenser (K) and/or the postcondenser may, for example, be configured as a plate apparatus and be integrated into the column jacket, preferably into the top of the column. To prevent solids formation, it may be advantageous to control the temperature of the condenser of the column, for example to temperatures of about 30 to about 50° C.

The top product precipitated in the condenser (K) is buffered in the distillate vessel (DB) and fed back to the column as the column return stream (i) by means of the return pump (RP). If required, a distillate fraction (j) can also be obtained therefrom. In the case of integration of the condenser into the top of the column, it is possible to dispense with the distillate vessel (DB) and the return pump (RP).

The bottom stream is advantageously fed to the bottom evaporator (SV) via the circulation pump (UP), which is preferably configured as a falling film evaporator. The bottoms discharge (g) of the column (TK) can also be withdrawn from this pumped circulation stream. Advantageously, the bottom stream (high boiler fraction) of the column can be withdrawn as a liquid stream (h) downstream of the bottom evaporator, optionally with the aid of a smaller pump (SP).

The bottom evaporator used for the dividing wall column may advantageously be a thin film apparatus, for example a falling film evaporator.

The product of value can be drawn off as a liquid side draw, stream (f), from the withdrawal section of the dividing wall column (TK). It is also possible, if required, to withdraw the product of value stream (f) as a gaseous draw stream, in which case, however, a further condenser is typically required. Owing to the melting point of L-menthol in pure or enriched form between 41 and 44° C., it is advantageous to insulate all product-conducting apparatuses (as well as the column, also all vessels and pumps) and lines, and preferably all apparatuses and lines of the vacuum system, i.e. to insulate them thermally with suitable materials and to provide them with trace heating. For example, electrical heating lines enclosed in the pipes, which are controlled with suitable instruments to temperatures of up to 70° C., preferably of 45 to 70° C., even more preferably to temperatures up to 60° C., especially preferably of 45 to 60° C., are advantageous here. Alternatively, it is also possible to use conventional trace heating systems, for example jacketed tubes with warm water flowing through the jacket.

The upper combined subregion (1) of the column has typically 5 to 50%, the rectifying section (2) of the feed section of the column 5 to 50%, the stripping section (4) of the feed section of the column 2 to 50%, the stripping section (2) of the withdrawal section of the column 5 to 50%, the rectifying section (5) of the withdrawal section 2 to 50%, and the combined lower section (6) of the column 5 to 50%, of the total number of theoretical plates of the column, where the percentages selected must add up to 100%.

Preferably, the upper combined subregion (1) of the column has 10 to 25%, the rectifying section (2) of the feed section of the column 15 to 30%, the stripping section (4) of the feed section of the column 15 to 30%, the stripping section (2) of the withdrawal section of the column 15 to 30%, the rectifying section (5) of the withdrawal section 15 to 30%, and the combined lower section (6) of the column 10 to 25%, of the total number of theoretical plates of the column, where the percentages selected must add up to 100%.

The sum of the number of theoretical plates of subregions (2) and (4) in the feed section is preferably 80 to 110%, more preferably 95 to 105%, of the sum of the number of plates of subregions (3) and (5) in the withdrawal section.

In a preferred embodiment of the process according to the invention, the feed point and the side draw point, with regard to the position of the theoretical plates, are arranged at different heights in the column, by virtue of the feed point being arranged 1 to 40, preferably 5 to 20, theoretical plates higher or lower than the side draw point.

It has additionally been found to be advantageous when the subregion of the column which is divided by the dividing wall and consists of the subregions (2), (3), (4) and (5) or sections thereof is equipped with structured packings or random packings (for example fabric packings such as Montz A3-500, Sulzer BX or CY or sheet metal packings such as Montz B1-500 (from Montz) or Mellapak (from Sulzer).

The vapor stream at the lower end of the dividing wall can be adjusted through the selection and/or dimensions of the separating internals and/or the incorporation of devices which generate a pressure drop, for example of restrictors, such that the ratio of the vapor stream in the feed section to that of the withdrawal section is 0.8 to 1.2, preferably 0.9 to 1.1.

The liquid effluxing from the upper combined section (1) of the column is advantageously collected in a collecting space arranged within the column or outside the column and is divided in a controlled manner by a fixed setting or control system at the upper end of the dividing wall such that the ratio of the liquid stream to the feed section to that to the withdrawal section is 0.1 to 2.0 in the case of a primarily liquid feed, and 1.0 to 2 in the case of a gaseous feed. The liquid feed is preferred in accordance with the invention.

The liquid effluxing from the upper combined subregion (1) to the feed section can be conveyed by means of a pump or introduced under quantitative control via a static feed head of at least 1 m, preferably by means of a closed-loop control system in conjunction with the liquid level control system of the collecting space. The control system is preferably adjusted such that the amount of liquid introduced to the feed section cannot fall below 30% of the desired normal value. In addition, the division of the liquid effluxing from the subregion (3) in the withdrawal section of the column to the side draw and to the subregion (5) in the withdrawal section of the column is advantageously adjusted by means of a control system such that the amount of liquid introduced to the subregion (5) cannot fall below a level of 30% of the desired normal value. The normal values are advantageously assumed to be twice to four times the amount, based on the feed rate.

The dividing wall column preferably has, at the upper and lower ends of the dividing wall, sampling means; samples can be taken in liquid or gaseous form from the column, continuously or at time intervals, and can be examined with regard to their composition, preferably by gas chromatography.

The division ratio of the liquid at the upper end of the dividing wall is preferably adjusted such that the concentration of those components of the high boiler fraction for which a particular concentration limit is to be achieved in the side draw (specifically isomenthol) in the liquid at the upper end of the dividing wall makes up 10 to 80% of the value which is to be achieved in the side draw product. The liquid division should preferably be adjusted to the effect that more liquid is passed to the feed section at higher contents of components of the high boiler fraction, and less liquid at lower contents of components of the high boiler fraction.

The heating output in the evaporator (SV) is preferably adjusted such that the concentration of those components of the low boiler fraction for which a particular concentration limit is to be achieved in the side draw (specifically neoisomenthol) is such at the lower end of the dividing wall that the concentration of components of the low boiler fraction in the liquid at the lower end of the dividing wall amounts to 10 to 80% of the value which is to be achieved in the side draw product. The heating output is advantageously adjusted to the effect that the heating output is increased at a higher content of components of the low boiler fraction, and the heating output is reduced at a lower content of components of the low boiler fraction.

The distillate withdrawal, i.e. the withdrawal of the low-boiling by-products, is preferably effected under temperature control or else under quantitative control, depending on the amount of the lower-boiling secondary components which are present in the feed mixture and are to be removed. The control temperature used is advantageously a measurement site in the subregion (1) of the column which is arranged 3 to 10, preferably 4 to 6, theoretical plates below the upper end of the column.

The bottom product is preferably withdrawn under temperature control or else under quantitative control, depending on the feed rate.

The withdrawal of the menthol, preferably L-menthol, process product obtained as the side product in pure or enriched form is preferably effected under level control, the control parameter used preferably being the liquid level in the column bottom.

The feed stream of the menthol-containing substance mixture for use in accordance with the invention is preferably partly or completely pre-evaporated and fed to the column in biphasic form or in the form of a gaseous stream and of a liquid stream.

In a preferred embodiment, in the context of the process according to the invention, a dividing wall column is used, the dividing wall of which is not welded into the column but is configured in the form of loosely inserted and adequately sealed subsegments.

The liquid division in the individual subregions of the column can preferably be adjusted inhomogeneously in a controlled manner, the liquid being introduced to an increased extent in the wall region especially in subregions (2) and (5), and being introduced to a reduced extent in the wall region in subregions (3) and (4).

The division ratio of the return liquid between withdrawal side and feed side of the dividing wall is preferably about 1:1 to about 3:1, preferably about 1:1 to about 2:1.

The position of the dividing wall in the individual subregions of the column can advantageously be adjusted such that the cross sections of feed and withdrawal sections have different areas.

The L-menthol in pure or enriched form obtainable in accordance with the invention can be obtained continuously via the side draw, or, in the case that further side draws are provided, via the middle side draw (f), and has, in a preferred embodiment, a menthol content of more than 99.5% by weight, preferably of 99.5 to 99.95% by weight, and a content of the other diastereomers of menthol as described above of up to 0.3% by weight (based in each case on the product obtained), possibly in addition to very small amounts of further impurities.

In a further preferred embodiment, the menthol obtained in accordance with the invention, preferably L-menthol in pure or enriched form, preferably in pure form, has a content of isopulegol and the diastereomers thereof as described above of up to 0.5% by weight in total, preferably up to 0.3% and more preferably up to 0.1% by weight (based on the product obtained). In a further preferred embodiment, the menthol obtained in accordance with the invention, preferably L-menthol in pure or enriched form, preferably in pure form, has a content of menthone and isomenthone of up to 0.5% by weight, preferably up to 0.3% and more preferably up to 0.1% by weight (based on the product obtained).

In a further aspect, the present invention relates to a system for performing the continuous process, as described above, for preparing racemic or optically active menthol in pure or enriched form.

The inventive system is shown in FIG. 1 and comprises a dividing wall column (TK) with 50 to 300 theoretical plates and one or more side draw points, which has a dividing wall (T) in the longitudinal direction of the column to form an upper combined column region (1), a lower combined column region (6), a feed section (2, 4) with a rectifying section (2) and stripping section (4), and a withdrawal section (3, 5) with a stripping section (3) and rectifying section (5), wherein all product-conducting constituents of the system (as well as the column, also all vessels, pumps and lines) and preferably all apparatuses and lines of the vacuum system are thermally insulated with suitable materials and provided with trace heating.

As already described above, electrical heating lines enclosed in the tubes, for example, are advantageous, which are controlled with suitable instruments to temperatures of up to 70° C., preferably of 45 to 70° C., even more preferably to temperatures up to 60° C., especially preferably of 45 to 60° C. Alternatively, it is also possible to use conventional trace heating systems, for example jacketed tubes with warm water flowing through the jacket.

The examples which follow serve to illustrate the invention, without restricting it in any way:

Example 1

A laboratory dividing wall column was constructed from five glass sections, each of length 1.2 m, with internal diameter 64 mm. A dividing wall made of sheet metal was inserted into the three middle sections. Above and below the dividing wall region, laboratory packings (Sulzer CY) were installed and, in the dividing wall region, metal fabric rings made of stainless steel with diameter 5 mm. In separating performance measurements which were performed with xylene isomer mixtures at a top temperature of 60 mbar, an overall separating performance of 100 theoretical plates over the entire column and about 55 theoretical plates in the dividing wall region was measured. The total number of theoretical plates present was thus about 155. The column was equipped with an oil-heated thin film evaporator (0.1 m$^2$) and a condenser cooled with cooling water.

Temperatures at different levels in the column and the top pressure and the pressure drop over the column were measured by means of a measurement recording system. The column possessed flow meters in the inlets and outlets, and a return flow meter, the measurement of which served as the control parameter for the inlet temperature of the oil thermostat. This control system ensured a constant return rate, which also established a constant pressure difference. The division of the amount of liquid above the dividing wall between feed section and withdrawal section of the dividing wall was achieved by means of a swivel funnel on a time cycle.

In the middle of the column at a height of 331 cm from the feed section of the dividing wall, 1000 g/h of liquid menthol of plant origin was fed to the column, which had been preheated to 90° C. and comprised 99.58 GC area % menthol, 0.22 GC area % isopulegol, 0.11 GC area % neomenthol and 0.03 GC area % isomenthol, and also 0.02 GC area % neoisomenthol. The column was operated at top pressure 50 mbar and a return rate of 3.0 kg/h. A pressure drop of about 34 mbar (±1 mbar) was established. At the top of the column, a temperature of 121° C. was measured, and in the bottom a temperature of 135° C. (±0.5 K). By means of a balance control system, the bottom draw was fixed to 2 g/h (±1 g/h) and the distillate withdrawal to 4 g/h (±1 g/h). The reflux ratio was thus about 750:1. The condenser of the column was at a temperature of 25° C. in order to prevent solids formation.

The liquid was divided above the dividing wall in a ratio of 1:1 (feed: withdrawal section). At a level of 300 cm in the withdrawal section of the dividing wall, a gaseous side draw (f) was withdrawn and condensed in a glass condenser, from which, depending on the bottom fill level, about 992 to 995 g/h of pure product were withdrawn by means of a pump.

The fractions obtained were analyzed by gas chromatography with the aid of a standard GC. Sample preparation: The (solidified) sample was heated to about 50° C. with melting and dissolved in toluene. The toluenic solution was injected into the gas chromatograph; in the integration, the toluene peak was correspondingly excluded.

Gas chromatography analyses were performed by the following method:
50 m CP-Wax 52 CB, ID.: 0.32 mm, FD.: 1.2 μm; injector: 200° C.; detector: 250° C.; 80° C.-3° C./min to 200° C., −10° C./min to 230° C./15 min;
$t_R$ (isopulegol): 30.07 min; $t_R$ (neomenthol): 31.08 min; $t_R$ (neoisomenthol): 32.5 min; $t_R$ (menthol): 32.8 min; $t_R$ (isomenthol): 33.8 min The pure product obtained at the side draw comprised, as well as 99.94 GC area % L-menthol, also 0.02 GC area % isomenthol and traces of other menthol diastereomers. In the bottom draw, 96.12 GC area % L-menthol was determined by GC analysis; the distillate comprised 44.7 GC area % L-menthol, 33.9 GC area % isopulegol, 12.9 GC area % neomenthol and 2.02 GC area % neoisomenthol. The distillation yield at the side draw was thus more than 99%.

Example 2

In the middle of the column at a height of 331 cm, 900 g/h of liquid L-menthol of synthetic origin were fed to the dividing wall column in the feed section of the dividing wall, which had been obtained by catalytic hydrogenation of L-isopulegol over a nickel catalyst, and comprised 99.39 GC area % L-menthol, 0.29 GC area % isopulegol, 0.25 GC area % neomenthol and 0.011 GC area % isomenthol, and also 0.044 GC area % neoisomenthol. The column was operated at top pressure 50 mbar and a return rate of 3.0 kg/h. A pressure drop of about 35 mbar (±1 mbar) was established. At the top of the column, a temperature of 120° C. was measured, and in the bottom a temperature of 135° C. (±0.5 K). The column was operated without a bottom draw and the distillate withdrawal was adjusted by means of a balance control system to 15 g/h (±1 g/h). The reflux ratio was thus about 200:1. The condenser of the column was at a temperature of 40° C. in order to prevent solids formation.

The liquid was divided above the dividing wall in a ratio of 1:1 (feed: withdrawal section). At a level of 300 cm in the withdrawal section of the dividing wall, a gaseous side draw (f) was withdrawn and condensed in a glass condenser from which, depending on the bottom fill level, about 885 to 890 g/h of pure product were drawn off by means of a pump.

The pure product obtained at the side draw comprised, as well as 99.93 GC area % L-menthol, also 0.027 GC area % neomenthol and traces of other menthol diastereomers. The distillate which is also liquid at room temperature comprised 73.1 GC area % L-menthol, 13.5 GC area % isopulegol, 10.9 GC area % neomenthol and 1.79 GC area % neoisomenthol. The continuously operated column was supplied with 22.05 kg of feed within 24.5 h, and 21.6 kg of pure product were withdrawn at the side draw. The distillation yield at the side draw was thus above 98.5%.

Example 3

A further laboratory dividing wall column was constructed from three glass sections with internal diameter 43 mm. The middle column section with a total length of 105 cm was provided with a glass dividing wall of thickness about 1 mm which had been fused in a fixed manner. In the region of the dividing wall, the column is equipped with 1 m of Sulzer DX packing on the feed side and 0.9 m of DX packing on the withdrawal side. Above and below the dividing wall, glass sections of length 50 mm were used, each of which was equipped with 33 cm of Sulzer DX packings.

In separating performance measurements which were carried out with xylene isomer mixtures at a top pressure of 60 mbar, a total separating performance of about 32 theoretical plates over the entire column and about 18 theoretical plates in the dividing wall region was measured. The total number of theoretical plates present was thus about 50. The column was equipped with an oil-heated thin film evaporator (0.1 m²) and a condenser cooled with cooling water at a temperature of 25° C. The inlet and outlet were each present at the middle of the dividing wall and were each configured with heating. Return lines and bottom discharge lines were likewise provided with electrical trace heating.

The temperatures at different levels in the column, and also the top pressure and the pressure drop over the column, were measured by means of a measurement recording system. The column possessed flow meters in the inlets and outlets, and a flow meter with control of the return rate. This control system ensured a constant return rate, which also established a constant pressure difference. The division of the amount of liquid above the dividing wall between feed section and withdrawal section of the dividing wall was achieved by means of a swivel funnel on a time cycle.

In the middle of the column, 120 g/h of liquid, virtually racemic menthol of synthetic origin were fed continuously to the dividing wall column in the feed section of the dividing wall, which had been preheated to 80° C. and obtained by catalytic hydrogenation of isopulegol over a nickel catalyst, and comprised 85.1% by weight of menthol, 0.2% by weight of isopulegol, 3.4% by weight of neomenthol and 0.98% by weight of isomenthol, and 1.25 GC area % neoisomenthol. In addition, 1.5 GC % by weight of the hydrocarbon phenylcyclohexane was present.

The fractions obtained were analyzed by gas chromatography with the aid of a standard GC. Sample preparation: the (in some cases solidified) sample was heated to about 50° C. with melting and dissolved in toluene. The toluenic solution was injected into the gas chromatograph; in the integration, the toluene peak was correspondingly excluded. The internal standard used for the % by weight determination was diethylene glycol diethyl ether (weight approx. 10% of the total amount of sample).

Gas chromatography analyses were carried out by the following method:
50 m CP Wax 52 CB, ID.: 0.32 mm, FD.: 1.2 µm; injector: 200° C.; detector: 250° C.; 80° C.-3° C./min to 200° C., −10° C./min to 230° C./15 min;

$t_R$ (diethylene glycol diethyl ether): 23.0 min; $t_R$ (isopulegol): 30.07 min; $t_R$ (neo-menthol): 31.08 min; $t_R$ (neoisomenthol): 32.5 min; $t_R$ (menthol): 32.8 min; $t_R$ (iso-menthol): 33.8 min; $t_R$ (phenylcyclohexane): 35.2 min The column was operated at top pressure 18 mbar and a return rate of 850 g/h. A pressure drop of about 3 mbar was established. At the top of the column, a temperature of 101° C. was measured, and in the bottom a temperature of 105° C. (±0.5 K). The column was operated with bottom draw rate 15 g/h (±2 g/h), and the distillate withdrawal was adjusted by means of a balance control system to 50 g/h (±5 g/h). The reflux ratio was thus about 17:1. The condenser of the column was at a temperature of 25° C., in order to prevent solids formation.

The liquid was divided above the dividing wall in a ratio of 3:4 (feed: withdrawal section). In the middle of the withdrawal section of the dividing wall, a liquid side draw (f) of about 55 g/h (±5 g/h) was withdrawn with the aid of a membrane pump.

The pure product obtained at the side draw comprised, as well as 98.2% by weight of menthol, also 0.14% by weight of neomenthol and 0.92 GC % by weight of isomenthol and 0.25 GC area % of neoisomenthol and about 0.45% by weight of phenylcyclohexane. The pure product had a specific rotation of −0.9 grd/(ml*g) (determination to USP30/NF25 "menthol").

The distillate which was also liquid at room temperature comprised 79.6% by weight of menthol, 0.67 GC % by weight of isopulegol, 6.9 GC % by weight of neomenthol and 2.5 GC area % of neoisomenthol, and also 3.0% by weight of phenylcyclohexane. In the bottoms, as well as 85.7% by weight of menthol, 2.9% by weight of isomenthol was also measured.

Comparative Example 1

In a glass laboratory column equipped with 1 m of Sulzer DX packing (about 20 theoretical plates) with an internal diameter of 50 mm, which is equipped with a boiler and a thin film evaporator (0.05 m²) in a pumped circulation system, 614 g of a synthetically produced L-menthol with 98.0 GC area % L-menthol, 1.69 GC area % isopulegol and 0.33 GC area % neomenthol were distilled batchwise at a top pressure of 50 mbar. The condenser of the column was operated with water at a temperature of 40° C.

The temperatures at the top of the column were between 122 and 123° C., and the bottom temperature was between 124° C. at the start and 125° C. toward the end of the distillation. The distillate vessel was electrically heated to about 60° C. in order to prevent solidification of the fraction. At a reflux ratio of 15:1, 3 fractions (31, 45 and 138 g) were obtained, and at a reflux ratio of 10:1 a further distillate fraction of 116 g. The first fraction obtained comprised 75.5 GC area % L-menthol, 19.6 GC area % isopulegol and 3.01 GC area % neomenthol, and also remained liquid at room temperature. The second fraction comprised 90.6 GC area % menthol, 7.03 GC area % isopulegol and 1.49 GC area % neomenthol, and the third correspondingly 98.09 GC area % L-menthol, 0.98 GC area % isopulegol and 0.3 GC area % neomenthol. In the fourth fraction, a menthol purity of 99.52 GC area % was finally achieved. 197 g of residue were isolated from the boiler, with 98.5 GC area % L-menthol.

The invention claimed is:

1. A continuous process for preparing racemic or optically active menthol of the formula (I)

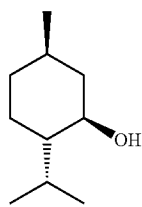

(I)

in pure or enriched form by distillatively separating racemic or optically active menthol from substance mixtures comprising racemic or optically active menthol and diastereomers of menthol, wherein the distillative separation is performed in a dividing wall column with 50 to 300 theoretical plates and one or more side draw points at an absolute operating pressure of 5 to 500 mbar, wherein all product-conducting lines, vessels and apparatuses connected to the dividing wall column, and all apparatuses and lines of the vacuum system, are thermally insulated and equipped with a temperature-controllable trace heating system.

2. The process according to claim 1, for preparing racemic or optically active menthol in pure or enriched form by distillatively separating racemic or optically active menthol from substance mixtures comprising racemic or optically active menthol and diastereomers of menthol, and also isopulegol of the formula (II)

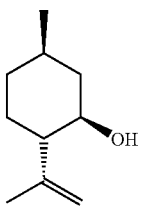

(II)

and/or diastereomers thereof, with or without menthones of the formula (III) and/or (IV)

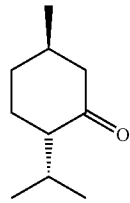

(III)

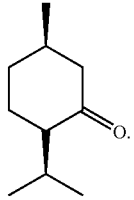

(IV)

3. The process according to claim 1, for preparing L-menthol in pure or enriched form by distillatively separating L-menthol from substance mixtures comprising L-menthol and diastereomers of menthol.

4. The process according to claim 1, wherein a substance mixture with a menthol content based on the overall mixture of 85 to 99.9% by weight is used.

5. The process according to claim 1, wherein menthol is obtained with a content of 99.5 to 99.95% by weight.

6. The process according to claim 1, wherein the menthol obtained in pure or enriched form has a content of isopulegol and diasteromers thereof of up to 0.5% by weight in total.

7. The process according to claim 1, wherein the resulting menthol in pure or enriched form has a menthone and/or isomenthone content of up to 0.5% by weight in total.

8. The process according to claim 1, wherein the distillative separation in the dividing wall column is performed at an absolute operating pressure of 20 to 100 mbar.

9. The process according to claim 1, wherein the distillative separation is performed in a dividing wall column with 100 to 180 theoretical plates.

10. The process according to claim 1, wherein the dividing wall column is operated at an absolute top pressure of 10 to 60 mbar and at an absolute bottom pressure of 30 to 100 mbar.

11. The process according to claim 1, wherein the dividing wall column used is a packed column with structured sheet metal or fabric packings with a specific surface area of about 100 to 750 m²/m³.

12. The process according to claim 1, wherein a dividing wall column (TK) is used, which has a dividing wall (T) in the longitudinal direction of the column to form an upper combined column region, a lower combined column region, a feed section with a rectifying section and stripping section, and a withdrawal section with a stripping section and rectifying section.

13. The process according to claim 1, wherein the menthol-comprising substance mixture (a) which serves as a feedstock is fed into the middle region of the feed section, the menthol in pure or enriched form is obtained as a liquid or gaseous side draw from the middle region of the withdrawal section, and one or more low boiler fractions are removed from the upper combined column region, and one or more high boiler fractions from the lower combined column region.

14. The process according to claim 1, wherein the dividing wall column is equipped with a falling film evaporator, and a high boiler fraction in liquid form is discharged downstream of the falling film evaporator.

15. The process according to claim 1, wherein the heat carrier medium used to cool the condenser and/or the post-condenser of the dividing wall column has a temperature controllable within a temperature range from 0 to 60° C.

16. A system for continuously preparing racemic or optically active menthol in pure or enriched form according to claim 1, comprising a dividing wall column (TK) with 50 to 300 theoretical plates and one or more side draw points, which has a dividing wall (T) in the longitudinal direction of the column to form an upper combined column region, a lower combined column region, a feed section with a rectifying section and stripping section, and a withdrawal section with a stripping section and rectifying section, wherein all product-conducting constituents of the system.

* * * * *